(12) United States Patent
Kuo et al.

(10) Patent No.: US 8,165,665 B2
(45) Date of Patent: *Apr. 24, 2012

(54) CHIP FOR SENSING A PHYSIOLOGICAL SIGNAL AND METHOD FOR SENSING THE SAME

(75) Inventors: Bo-Jau Kuo, Taipei (TW); Ching-Hsiu Yang, Taipei (TW)

(73) Assignee: National Yang Ming University, Taipei (TW)

( * ) Notice: Subject to any disclaimer, the term of this patent is extended or adjusted under 35 U.S.C. 154(b) by 346 days.

This patent is subject to a terminal disclaimer.

(21) Appl. No.: 12/408,021

(22) Filed: Mar. 20, 2009

(65) Prior Publication Data

US 2010/0125184 A1    May 20, 2010

(30) Foreign Application Priority Data

Nov. 19, 2008   (TW) .............................. 97144780 A

(51) Int. Cl.
*A61B 5/0402* (2006.01)

(52) U.S. Cl. ...................................................... 600/509

(58) Field of Classification Search .................. 607/508, 607/509, 516, 517; 600/508, 509, 516, 517, 600/515

See application file for complete search history.

(56) References Cited

U.S. PATENT DOCUMENTS

| | | | | |
|---|---|---|---|---|
| 4,680,708 A | * | 7/1987 | Ambos et al. | 600/509 |
| 4,905,706 A | * | 3/1990 | Duff et al. | 600/514 |
| 4,974,598 A | * | 12/1990 | John | 600/509 |
| 5,437,285 A | * | 8/1995 | Verrier et al. | 600/515 |
| 6,148,228 A | * | 11/2000 | Fang et al. | 600/509 |
| 2004/0181159 A1 | * | 9/2004 | Kuo et al. | 600/509 |

* cited by examiner

*Primary Examiner* — Eric D. Bertram
*Assistant Examiner* — Roland Dinga
(74) *Attorney, Agent, or Firm* — Muncy, Geissler, Olds & Lowe, PLLC

(57) ABSTRACT

A chip for sensing a physiological signal comprises: an input unit for receiving a first electrocardiogram (ECG) signal; a filter for generating a second ECG signal by filtering the first ECG signal; an amplifying unit for generating a third ECG signal by amplifying the second ECG signal; an Analog-to-Digital converting unit for converting the third ECG signal into a digital signal; an operating unit for generating a plurality of analysis data by operational analyzing the digital signal; and an output unit for outputting the plurality of analysis data. Therefore, the manufacturing cost of the chip is decreased and the chip is suitable for use in small-scale devices.

15 Claims, 5 Drawing Sheets

| EKG<br><br>〜┤┤┤┤〜<br><br>$A_P, A_Q, A_R, A_S, A_T\ T_{P-R},$<br>$T_{Q-T}, T_{Q-S}$ | HR=72<br>THRV parameter :<br>SD=22<br>SDNN=   SDANN=<br>RMSSD=  SDNN index=<br>SDSD=   pNN50 =<br>NN50 count= |
|---|---|
| RR<br><br>〜〜〜〜 | TP= VLF= LF= HF=<br>LF/HF= LF%= HF%=<br><br>MPSD<br><br>　　　　Frequency |

FIG. 4

CHIP FOR SENSING A PHYSIOLOGICAL SIGNAL AND METHOD FOR SENSING THE SAME

BACKGROUND OF THE INVENTION

1. Field of the Invention

The present invention relates to a physiological signal sensing device, and more particularly, to a chip with its sensing method that is easy to operate for sensing physiological signals and improving the accuracy of records for electrocardiogram (ECG).

2. Description of the Related Art

It is known that the heart is an organ composed by muscles. However, the muscle that composes heart is different than other muscles (striated muscle, such as arms, legs, chest muscles). It is called "myocardium". When the heart is active, current is generated by heart beating and electrocardiogram (ECG) is a picture that records the change of this current. From ECG, we can diagnose the shape changes of heart caused by arrhythmia and all kinds of heart diseases. From the changes of ECG, we can know whether the heart beating is regulative or not (i.e. arrhythmia). The main reason of causing arrhythmia is when there is a problem at a certain part or point of conduction system in heart. From the changes of different ECG pictures, we can understand which point of the conduction system is abnormal. In addition to the conduction system diseases, the changes of electrocardiogram follow the heart shape changed by whatever reasons. For example, when the workload of the heart is increased by long-term high blood pressure or heart valve diseases, myocardium hypertrophies will be thickened to cope with the increased workload. Meanwhile, the current of heart is also changed so as to change the shape of ECG. Therefore, from the changes of ECG, we can know if there is myocardium hypertrophy and also indirectly know if there is any cardiac disease to increase the workload of myocardium.

The present electrocardiogram or heart rate variability analysis facilities all complete the analysis and the collection of the electrocardiogram by customized lines and a customized program. These customized lines are comprised of complex amplifier circuit, and the analysis programs which are expensive and customized as well have to run in the very expensive PC or workstation. The price of hardware-related is often more than ten thousand NTD, and the price of computer is above twenty thousand NTD. The range of the price of software is large, which can range from two thousand to one million NTD. The total cost is extremely high, which would cause serious limit and impact on extension and application of this technology.

Because most of the electrocardiogram measuring instruments are very expensive and the size is large, most of the ECG is operated in hospitals; and very few people would like to purchase one to put at home. It would cause inconvenience to the people. Therefore, it is desirable to let people gain their own ECG correctly at any time without going to a hospital, which is a useful direction of thinking.

SUMMARY OF THE INVENTION

An object of the present invention is to provide a chip for sensing a physiological signal and method for sensing the same in order to reduce the manufacturing cost and suitable for use in small-scale devices.

In order to concretely describe the present invention, a chip for sensing a physiological is provided, which includes:
an input unit for receiving a first electrocardiogram (ECG) signal;
a filter unit for generating a second ECG signal by filtering the first ECG signal;
an amplifying unit for generating a third ECG signal by amplifying the second ECG signal;
an analog to digital conversion unit for converting the third ECG signal to a digital signal;
an operating unit, comprising:
  a QRS wave sieving unit for sieving a plurality of consecutive QRS waves from the digital signal;
  a heart beat measurement unit for generating a heartbeat cycle signal according to the QRS waves;
  a time-domain analysis unit for generating a time-domain analysis data according to the heartbeat cycle signal;
  a Fourier analysis unit for generating a Fourier analysis data, according to the heartbeat cycle signal;
  a PQRST wave sieving unit for sieving a plurality of consecutive PQRST waves from the digital signal; and
  a PQRST wave analysis unit for generating a ECG analysis data according to the PQRST waves; and
an output unit for outputting the time-domain analysis data, the Fourier analysis data and the ECG analysis data.

According to another embodiment, the present invention provides a sensing method of a physiological sensing device, comprising the steps of:
receiving a first ECG signal;
generating a second ECG signal after filtering the first ECG signal;
generating a third ECG signal after amplifying the second ECG signal;
converting the third ECG signal into a digital signal;
sieving a plurality of consecutive QRS waves from the digital signal;
generating a heartbeat cycle signal according to the QRS waves;
generating a time-domain analysis data according to the heartbeat cycle signal;
generating a Fourier analysis data according to the heartbeat cycle signal;
sieving a plurality of consecutive PQRST waves from the digital signal;
generating a ECG analysis data according to the PQRST waves; and
outputting the time-domain analysis data, the Fourier analysis data and the ECG analysis data.

In order to better describe the features and advantages of the present invention mentioned above, embodiments will be provided below with reference to appended drawings to better describe the present invention.

BRIEF DESCRIPTION OF THE DRAWINGS

FIG. 4 is a display diagram of the analysis data according to the present invention.

DETAILED DESCRIPTION OF THE PREFERRED EMBODIMENTS

Figure 1:
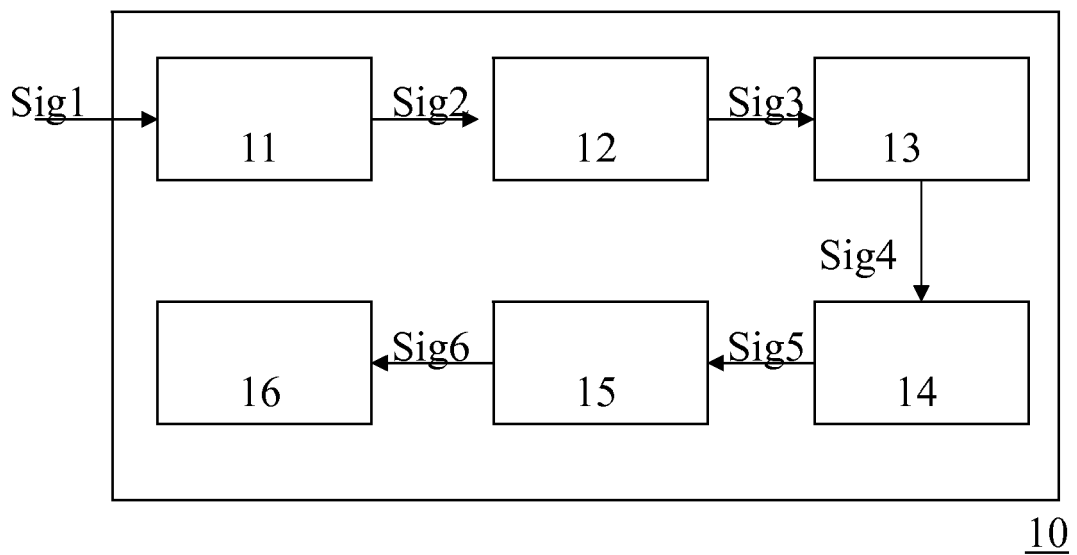
FIG. 1 is a function block diagram of the chip according to the present invention.

Each heartbeat cycle generates three distinct ECG (electrocardiogram) waves, which respectively are P wave (atrial depolarization, that is, potential difference generated by depolarization before the atrial contraction occur), QRS wave (ventricular depolarization, that is the beginning of the myocardial depolarization, which is the beginning of ventricular contraction) and T wave (ventricular re-polarization—when myocardial cells depolarize, they will be a period of time for refusing accept any further stimulation).

These waves are not action potential, but to represent the potential change between the two regions on the heart surface, which is an effect generated by mixing up a lot of the action potential of myocardial cells. For example, we can know that atrial depolarization generates a potential difference by up-deflection of ECG line; therefore, the up-deflection of ECG line reaches the maximum level when half of the atrial is depolarized. ECG line returns back to the baseline when all of the atrial depolarize because the whole atrium area is in the same polarity. Hence atrial depolarization causes P wave.

The action potential is transmitted to ventricular and establish a similar potential difference, which causes a rapid upward deflection ECG line, and then back to the baseline after the whole ventricular is polarized. Hence, the ventricular depolarization can be represented by QRS wave. The plain period of myocardial cells action potential is equivalent to ST-segment of ECG. Finally, T-wave is generated by the re-polarization of ventricular.

ECG waveforms and their appearing times might be affected by the transmission of electrical signals changes caused by many kinds of cardiac defects. That is why we must rely on ECG to diagnose some heart diseases. Autonomic nervous system controls the body and life to maintain the physiological functions including blood pressure, heart rate, trachea resistance, perspiration, body temperature, energy metabolism, and those nerve controls can be operated unconsciousness. Autonomic nervous system is divided into two major parts, sympathetic and parasympathetic nervous system. In general, the former is related to against environment, and the latter related to living and propagation.

For example, the excitement of former would raise blood pressure and dilates pupils, and the excitement of latter would facilitate the secretion of gastrointestinal and genital erection and so on.

In general, the sympathetic and parasympathetic nerve systems are both prosper in youth and both fading in old age. However, sympathetic nerve is stronger than parasympathetic nerve in male and vice versa in female. It is obvious that sympathetic and parasympathetic nerve systems have a close connection with daily work and rest of human body.

If the autonomic nervous is disorder, a variety of acute or chronic diseases might be caused, such as heart disease and high blood pressure and so on, that will in turn lead to a serious emergency case, such as sudden death. As a result, to keep autonomic nervous system healthy is an important issue in medicine.

In recent years, many new diagnostic techniques for autonomic nervous system have been successfully developed. Due to the maturity of computer technology and spectrum analysis, autonomic nervous system functions of heart can be detected and quantified through small changes in heart rate, that is, heart rate variability (heart rate variability, HRV) when a human body is in rest. In other words, we can analyze or diagnose a normal person's autonomic nervous system function without interfering in his daily routine.

Some method of computing heart rate variability is analysis in the time-domain such as The Standard Deviation of Normal to Normal Intervals, SDNN; and some are assisted by spectral analysis. Researchers found out that the fluctuate routes of the small fluctuations in heart rate variability can represent total power (TP). And those fluctuations may also be clearly divided into two groups, high-frequency (HF) and low-frequency (LF) components. In which the high frequency component synchronizes with animal's respiratory signal, so it is also known as the respiratory component. Low-frequency component is conjectured to have a connection with blood vessels movement and pressure sensing reflex. Some scholars further divide low-frequency component into very low frequency (VLF) and low-frequency components.

The present invention combines the amplifiers, analog circuits, digital computer and analysis programs (heart rate variability, parameters of PQRST waves and so on) being needed to measure ECG into a chip for reducing the manufacture cost. Moreover, because the chip size is small enough for using in small-scale devices, more and more people can be very conveniently in use the technology.

Figure 2:
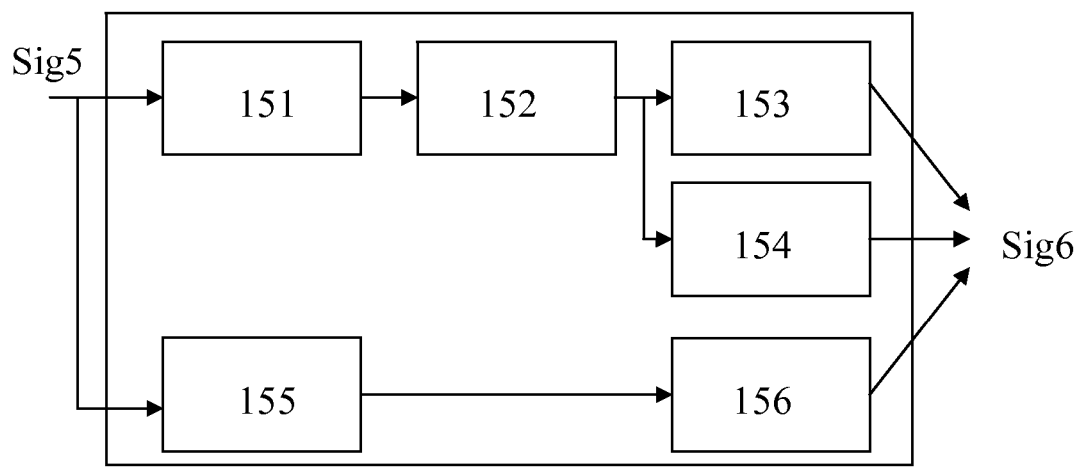
FIG. 2 is a function block diagram of the operating unit according to the present invention.

Referring to FIG. 1 and FIG. 2, the chip 10 for sensing a physiological signal of the present invention substantially consists of an input unit 11, a filter unit 12, an amplifying unit 13, an analog to digital conversion unit 14, an operating unit 15 and an output unit 16. The input unit 11 receives a first ECG signal Sig1 generated by a subject's (or a human being or a testee) heartbeat. The filter unit 12 filters the first ECG signal, Sig1 to generate a second ECG signal Sig2 and keep the second ECG signal Sig2 from the outside interference to generate noise. The amplifying unit 13 amplifies the second ECG signal Sig2 to generate a third ECG signal Sig3, so as to facilitate follow-up treatment. The analog to digital conversion unit 14 converts the third ECG signal Sig3 into a digital signal Sig4 (The first ECG signal Sig1 generated by user's heartbeat is analog and it is easy to compute after converting into digital signal). The operating unit 15 processes the digital signal through a series of operations to generate a plurality of analysis data Sig6, which are output by an output unit 16.

The operating unit 15 substantially consists of a QRS wave sieving unit 151, a heartbeat cycle measurement unit 152, a time domain analysis unit 153, a Fourier analysis unit 154, a PQRST wave sieving unit 155 and a PQRST wave analysis unit 156. QRS wave sieving unit 151 sieves a plurality of consecutive QRS waves from the digital signal. The heartbeat cycle measurement unit 152 generates a heartbeat cycle signal based on the QRS waves. The time-domain analysis unit 153 generates a time-domain analysis data based on the heartbeat cycle signal. The Fourier analysis unit 154 generates a Fourier analysis data based on the heartbeat cycle signal. The PQRST wave sieving unit 155 sieves a plurality of consecutive PQRST waves from the digital signal and the PQRST wave analysis units 156 generates an ECG analysis data based on the PQRST waves. The Time-domain analysis data, the Fourier analysis data and the ECG analysis data are the basic data of the analysis data Sig6.

Figure 3:
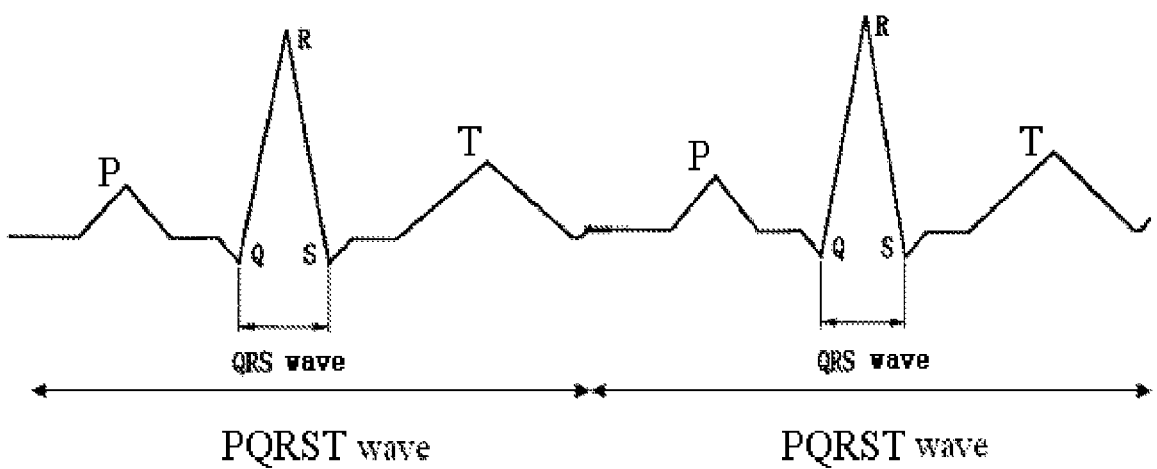
FIG. 3 is the wave diagram of the present invention.

Referring to FIG. 3 and FIG. 2, the QRS wave sieving unit 151 sieves two consecutive digital signals Sig4 to two QRS waves, that is, two heartbeat signal of the subject. The heartbeat cycle measurement unit 152 measures the intervals of R-R wave between two QRS waves for generating the heartbeat cycle signal, and the time-domain analysis unit 153 as well as Fourier analysis unit 154 are in accordance with the heartbeat cycle signal to process calculation.

The time domain analysis unit 153 carrys out the analysis of the heartbeat cycle such as standard deviation of all NN intervals, SDNN, Standard deviation of the averages of NN intervals in all 5-minute segments of the entire recording, SDANN, the square root of the mean of the sum of the squares of differences between adjacent NN intervals, RMSSD, mean of the standard deviations of all NN intervals for all 5-minute segments of the entire recording, SDNN index, standard deviation of differences between adjacent NN intervals, SDSD, number of pairs of adjacent NN intervals differing by more than 50 ms in the entire recording, NN50 count, NN50 count divided by the total number of all NN intervals, pNN50 to generate the time domain analysis data. The time-domain analysis data will be generated and showed on the output unit 16 in FIG. 4.

The Fourier analysis unit 154 carries out the analyses of heart rhythm cycle signal for power spectrum density of the total power (Total power of HPSD, TP), extremely low frequency rhythm power spectrum density (Very low frequency of HPSD, VLF), low-frequency rhythm power spectrum density (Low frequency power, LF), high-frequency heart-power spectrum density (High frequency power, HF), high-frequency low-ratio (Low frequency power to HF ratio, LF/HF), low-frequency standard (normalized LF, LF %), high-frequency standard (normalized HF, HF %) to generate the Fourier analysis data as shown on the output unit 16 in FIG. 4.

The PQRST wave sieving unit 155 sieves the digital signal Sig4 into one or more PQRST waves. The PQRST wave analysis units 156 will be calculated according to the PQRST, as well as the high point of time (such as P point height ($A_P$), Q point height ($A_Q$), R point height ($A_R$), S point height ($A_S$), T point height ($A_T$), RR interval of time ($T_{PR}$), QT interval of time ($T_{QT}$), QS interval of time ($T_{QS}$)), and so on to generate an ECG analysis data displayed on the output unit 16 as shown in FIG. 4.

The present combines all functions that ECG diagnosis needed into a chip, so that the chip can be integrated into portable electronic devices such as cell phones, PDAs, notebook computer and MP3 players for use. The only thing we should do is to install an electro-cardio detecting unit on the portable electronic devices for connecting to the subject and receiving the heartbeat signal of the subject. Further, the chip can be integrated into a physiological signal sensing device (carrying out electrocardiogram(ECG) or electromyography (EMG), body temperature and blood sugar detections, to detect a variety of physiological signals for the purpose of effectiveness) for use and output the analysis data on the display of the device aforementioned. As a result, people do not need to go to hospitals for measuring ECG data. The portable electronic devices can carry out and measure. It is very convenient and practical with low manufacturing costs.

Figure 5:
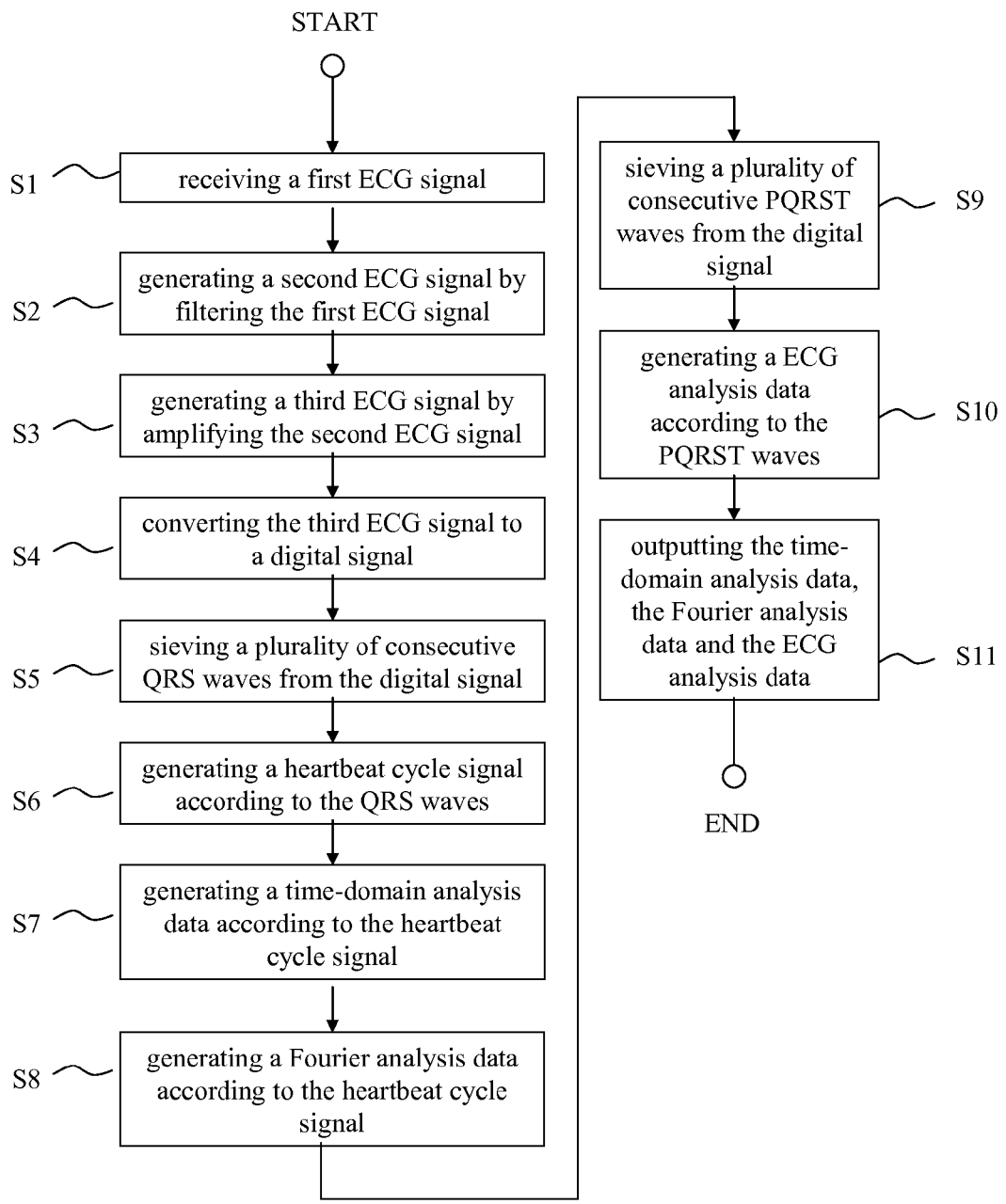
FIG. 5 is the implementation flow chart of the present invention.

Referring FIG. 5, the sensing method of a chip for sensing a physiological signal comprises the steps of: receiving a first ECG signal (S1), that is generated by the subject's heartbeats; then generating a second ECG signal (S2) by filtering the first ECG signal, such that the second ECG signal is kept from generating noise due to outside interference; and then generating a third ECG signal by amplifying the second ECG signal (S3), so as to facilitate follow-up treatment; then converting the third ECG signal to a digital signal (S4) (Due to the first ECG signal arising from the user's heart rate is analog, calculation is made easier after converting the signal into digital signal); and sieving a plurality of consecutive QRS waves from the digital signal (S5) from the consecutive digital signal; generating a heartbeat cycle signal according to the QRS waves (S6); generating a time-domain analysis data according to the heartbeat cycle signal (S7); generating a Fourier analysis data according to the heartbeat cycle signal (S8); sieving a plurality of consecutive PQRST waves from the digital signal (S9); generating a ECG analysis data according to the PQRST waves (S10); and outputting the time-domain analysis data, the Fourier analysis data and the ECG analysis data (S11) by a display unit built in a physiological sensing device.

Although the present invention has been disclosed above with the embodiments, they are not intended to limit the invention. Any ordinary skilled person in this field can make some modifications and improvement without departing from the spirit and scope of this invention. Therefore, the scope of this invention is defined by the appended claims.

What is claimed is:

1. A chip for sensing a physiological signal comprising:
   an input unit for receiving a first electrocardiogram (ECG) signal;
   a filter unit for generating a second ECG signal by filtering the first ECG signal;
   an amplifying unit for generating a third ECG signal by amplifying the second ECG signal;
   an analog to digital conversion unit for converting the third ECG signal to a digital signal;
   an operating unit, comprising:
      a QRS wave sieving unit for sieving a plurality of consecutive QRS waves from the digital signal;
      a heart beat measurement unit for generating a heartbeat cycle signal according to the QRS waves;
      a time-domain analysis unit for generating a time-domain analysis data according to the heartbeat cycle signal;
      a Fourier analysis unit for generating a Fourier analysis data, according to the heartbeat cycle signal, wherein the Fourier analysis unit carries out the analysis of one of heart rhythm cycle signal for power spectrum density of the total power, extremely low frequency rhythm power spectrum density, low-frequency rhythm power spectrum density, high-frequency heart-power spectrum density, high-frequency low-ratio, low-frequency standard, high-frequency standard to generate the Fourier analysis data;
      a PQRST wave sieving unit for sieving a plurality of consecutive PQRST waves from the digital signal; and
      a PQRST wave analysis unit for generating a ECG analysis data according to the PQRST waves; and
   an output unit for outputting the time-domain analysis data, the Fourier analysis data and the ECG analysis data.

2. The chip of claim 1, wherein the heartbeat cycle measurement unit measures the intervals of R-R waves between the two QRS waves for generating the heartbeat cycle signal.

3. The chip of claim 1, wherein the time-domain analysis unit carries out the analyses of one of the heartbeat cycle such as standard deviation of all NN intervals, Standard deviation of the averages of NN intervals in all 5-minute segments of the entire recording, the square root of the mean of the sum of the squares of differences between adjacent NN intervals, mean of the standard deviations of all NN intervals for all 5-minute segments of the entire recording, standard deviation of differences between adjacent NN intervals, number of pairs of adjacent NN intervals differing by more than 50 ms in the entire recording and NN50 count divided by the total number of all NN intervals to generate the time-domain analysis data.

4. The chip of claim 1, wherein the PQRST wave analysis unit generates the ECG analysis data by calculating high points of the PQRST wave and intervals between the high points.

5. The chip of claim 1, wherein the chip is integrated into a mobile phone, a PDA, a notebook computer or a MP3 player, and each of the mobile phone, PDA, notebook computer or MP3 player installs an electro-cardio detecting unit detecting unit.

6. The chip of claim 1, wherein the chip is integrated into a physiological signal sensing device.

7. The chip of claim 6, wherein the physiological signal sensing device carries out electromyography, body temperature and blood sugar detections.

8. A sensing method of a chip for sensing a physiological signal comprising the steps of:
   receiving a first ECG signal with an input unit;
   generating a second ECG signal after filtering the first ECG signal with a filter unit;
   generating a third ECG signal after amplifying the second ECG signal with an amplifying unit;
   converting the third ECG signal into a digital signal with an analog to digital conversion unit;
   sieving a plurality of consecutive QRS waves from the digital signal with a QRS wave sieving unit;
   generating a heartbeat cycle signal according to the QRS waves with a heart beat measurement unit;
   generating a time-domain analysis data according to the heartbeat cycle signal with a time-domain analysis unit;
   generating a Fourier analysis data according to the heartbeat cycle signal with a Fourier analysis unit, the Fourier analysis unit carrying out one of the analyses of heart rhythm cycle signal for power spectrum density of the total power, extremely low frequency rhythm power spectrum density, low-frequency rhythm power spectrum density, high-frequency heart-power spectrum density, high-frequency low-ratio, low-frequency standard and high-frequency;
   sieving a plurality of consecutive PQRST waves from the digital signal with a PQRST wave sieving unit;
   generating a ECG analysis data according to the PQRST waves with a PQRST wave analysis unit; and
   outputting the time-domain analysis data, the Fourier analysis data and the ECG analysis data with a output unit.

9. The method of claim 8, further comprising the step of measuring the intervals of R-R waves between the two QRS waves with the heartbeat cycle measurement unit.

10. The method of claim 8, further comprising step of carrying out one of the analyses of heartbeat cycle such as standard deviation of all NN intervals, Standard deviation of the averages of NN intervals in all 5-minute segments of the entire recording, the square root of the mean of the sum of the squares of differences between adjacent NN intervals, mean of the standard deviations of all NN intervals for all 5-minute segments of the entire recording, standard deviation of differences between adjacent NN intervals, number of pairs of adjacent NN intervals differing by more than 50 ms in the entire recording and NN50 count divided by the total number of all NN intervals to generate the time-domain analysis data with the time domain analysis unit.

11. The method of claim 8, further comprising the step of analyzing the height of P, Q, R, S and T points of the PQRST waves and intervals between each point with the PQRST wave analysis unit.

12. A sensing method of a chip for sensing a physiological signal wherein all the following process are performed by the chip; said processes including:
   receiving a first ECG signal;
   generating a second ECG signal after filtering the first ECG signal;
   generating a third ECG signal after amplifying the second ECG signal;
   converting the third ECG signal into a digital signal;
   sieving a plurality of consecutive QRS waves from the digital signal;
   generating a heartbeat cycle signal according to the QRS waves;
   generating a time-domain analysis data according to the heartbeat cycle signal;
   generating a Fourier analysis data according to the heartbeat cycle signal, the Fourier analysis unit carrying out one of the analyses of heart rhythm cycle signal for power spectrum density of the total power, extremely low frequency rhythm power spectrum density, low-frequency rhythm power spectrum density, high-frequency heart-power spectrum density, high-frequency low-ratio, low-frequency standard and high-frequency;
   sieving a plurality of consecutive PQRST waves from the digital signal;
   generating a ECG analysis data according to the PQRST waves; and
   outputting the time-domain analysis data, the Fourier analysis data and the ECG analysis data.

13. The method of claim 12, further comprising the step of measuring the intervals of R-R waves between the two QRS waves.

14. The method of claim 12, further comprising step of carrying out one of the analyses of heartbeat cycle such as standard deviation of all NN intervals, Standard deviation of the averages of NN intervals in all 5-minute segments of the entire recording, the square root of the mean of the sum of the squares of differences between adjacent NN intervals, mean of the standard deviations of all NN intervals for all 5-minute segments of the entire recording, standard deviation of differences between adjacent NN intervals, number of pairs of adjacent NN intervals differing by more than 50 ms in the entire recording and NN50 count divided by the total number of all NN intervals to generate the time-domain analysis data.

15. The method of claim 12, further comprising the step of analyzing the height of P, Q, R, S and T points of the PQRST waves and intervals between each point.

* * * * *